United States Patent [19]

Shen

[11] 3,949,082

[45] Apr. 6, 1976

[54] THIADIAZOLES AS ANTI-INFLAMMATORY AGENTS

[75] Inventor: Tsung-Ying Shen, Westfield, N.J.

[73] Assignee: Merck & Co., Inc., Rahway, N.J.

[22] Filed: July 24, 1974

[21] Appl. No.: 491,445

[52] U.S. Cl. ............................................. 424/270
[51] Int. Cl.² ...................................... A61K 31/425
[58] Field of Search.................. 424/270; 260/302 D

[56] References Cited
UNITED STATES PATENTS
3,419,575  12/1968  Griss............................ 424/270 X

*Primary Examiner*—Frederick E. Waddell
*Attorney, Agent, or Firm*—Mario A. Monaco; Harry E. Westlake, Jr.

[57] ABSTRACT

The invention relates to a method of treating inflammation employing 1,3,4-thiadiazole compounds and to pharmaceutical compositions thereof.

3 Claims, No Drawings

THIADIAZOLES AS ANTI-INFLAMMATORY AGENTS

SUMMARY OF THE INVENTION

This invention relates to the use of 2,5-bis ethylamino-1,3,4-thiadiazole and 2,5-bis allylamino-1,3,4-thiadiazole as medicinal agents. These compounds exhibit anti-inflammatory activity and also possess a useful degree of anti-pyretic and analgesic activity.

BACKGROUND OF THE INVENTION

There has been much research carried on in the past for development of anti-inflammatory drugs. As a result, a great many new drugs have been synthesized. Most of these have been steroids of the 11-oxygenated pregnane series. These, while highly effective, have the drawback of causing many side effects. There has also been a concentrated effort in anti-inflammatory research in indole, indene and phenylacetic acids among others with the result of many useful drugs. I have found that 2,5-bis ethylamino-1,3,4-thiadiazole and 2,5-bis allylamino-1,3,4-thiadiazole also are valuable anti-inflammatory agents.

DESCRIPTION AND PREFERRED EMBODIMENTS

This invention is directed to the use of known 2,5-bis ethylamino-1,3,4-thiadiazole and 2,5 bis allylamino-1,3,4-thiadiazole compounds as anti-inflammatory anti-pyretic and analgesic agents. The invention is also directed to pharmaceutical compositions employing these compounds.

The treatment of inflammation in accordance with the method of the present invention is accomplished by topically, orally, rectally or parenterally administering to patients 2,5-bis ethylamino-1,3,4-thiadiazole, 2,5-bis allylamino-1,3,4-thiadiazole or mixtures thereof in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin and acacia. Exemplary of liquid carriers are peanut oil, olive oil, seasame oil and water. Similarly, the carrier or diluent may include a time delay material such as glyceryl monostearate or glyceryl distearate alone or with a wax.

Several pharmaceutical forms of the therapeutically useful compositions can be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, an aqueous solution or a liquid suspension. Suppositories may be prepared in a conventional manner by mixing the compounds of this invention with a suitable non-irritating excipient which is solid at room temperature, but liquid at the rectal temperature. Such materials are cocoa butter and polyethylene glycol. Gels and lotions for topical application may be prepared in conventional manners.

The active compounds are administered in an amount sufficient to treat inflammation; that is, to reduce inflammation. Advantageously, the compositions will contain the active ingredient in an amount of from about 1 mg. to 100 mg. per kg. body weight per day (50 mg. to 5 g. per patient per day), preferably from about 3 mg. to 30 mg./kg. body weight per day (150 mg. to 1.5 g. per patient per day).

The method of treatment of this invention comprises administering to a patient (animal or human) the compound as previously described admixed with a non-toxic pharmaceutical carrier such as exemplified above. It should be understood that although preferred dosage ranges are given the dose level for any particular patient depends upon the activity of the specific compound employed. Also many other factors that modify the actions of drugs will be taken into account by those skilled in the art in the therapeutic use of medicinal agents, particularly those described above; for example, body weight, sex, diet, time of administration, route of administration, rate of excretion, drug combination, reaction sensitivities and severity of the particular disease.

Various tests in animals have been carried out to show the ability of the compounds described herein to exhibit reactions that can be correlated with anti-inflammatory activity in humans. One such test used is the carrageenin test which is known to correlate well with anti-inflammatory activity in humans and is a standard test used to determine anti-inflammatory activity. This test shows the ability of compounds to inhibit edema induced by injection of an inflammatory agent into the tissue of the foot of a rat against non-inflammed controls. This is outlined in detail by C. A. Winter, Proc. Soc. Exptl. Biolog, & Med., 1962, 111, 544. This correlation has been shown by the activities of compounds known to be clinically active, including Indocin, Aspirin, Butazolidin, Tandearil, Cortone, Hydrocortone, Decadron. In view of the results of this test, the instant compounds can be considered to be active anti-inflammatory agents. Another test used to show the ability of the instant compounds to inhibit edema is the Adjuvant arthritis test. This testing method is also known to correlate with anti-inflammatory activity in humans. The results of this test also show that the instant compounds can be considered active anti-inflammatory agents.

The following examples are presented to further illustrate the invention:

EXAMPLE 1

A mixture of 250 parts of 2,5-bis ethylamino-1,3,4-thiadiazole and 25 parts of lactose is granulated with water, and to this is added 100 parts of maize starch. The mass is passed through a 16 mesh screen. The granules are dried at a temperature below 60°C. The dry granules are passed through a 16 mesh screen, and mixed with 3.8 parts of magnesium stearate. They are then compressed into tablets suitable for oral administration.

25, 100 or 500 parts of 2,5-bis ethylamino-1,3,4-thiadiazole may be used in place of 250 parts above to produce tablets suitable for oral administration according to the method of this invention.

EXAMPLE 2

A mixture of 50 parts of 2,5-bis allylamino-1,3,4-thiadiazole, 3 parts of the calcium salt of lignin sulfonic acid and 237 parts of water is ball-milled until the size of substantially all of the particles is less than 10 microns. The suspension is diluted with a solution containing 3 parts of sodium carboxymethylcellulose and 0.9 parts of the butyl ester of p-hydroxy benzoic acid in 300 parts of water. There is thus obtained an aqueous suspension suitable for oral administration for therapeutic purposes.

2,5-bis ethylamino-1,3,4-thiadiazole may be used in place of the allylamino compound in the above example to obtain a suspension suitable for oral administration.

EXAMPLE 3

A mixture of 250 parts of 2,5-bis ethylamino-1,3,4-thiadiazole, 200 parts of maize starch and 30 parts of alginic acid is mixed with a sufficient quantity of 10% aqueous paste of maize starch and granulated. The granules are dried in a current of warm air, and the dry granules are then passed through a 16-mesh screen, mixed with 6 parts of magnesium stearate and compressed into tablet form to obtain tablets suitable for oral administration.

Similar results are obtained by employing 2,5-bis allylamino-1,3,4-thiadiazole in place of the ethylamino compound in the above example.

EXAMPLE 4

A mixture of 500 parts of 2,5-bis allylamino-1,3,4-thiadiazole, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

Similar results are obtained by employing 2,5-bis ethylamino-1,3,4-thiadiazole in place of the allylamino compound in the above example.

EXAMPLE 5

1. Tablets — 10,000 scored tablets for oral use, each containing 500 mg. of active ingredient are prepared from the following ingredients:

|  | Gm. |
|---|---|
| 2,5-bis ethylamino-1,3,4-thiadiazole | 5000 |
| Starch, U.S.P. | 350 |
| Talc, U.S.P. | 250 |
| Calcium stearate | 35 |

The thiadiazole is granulated with a 4% w./v. aqueous solution of methylcellulose U.S.P. (1500 cps.). To the dried granules is added a mixture of the remainder of the ingredients and the final mixture compressed into tablets of proper weight.

2. Capsules — 10,000 two-piece hard gelatin capsules for oral use, each containing 250 mg. of active ingredient are prepared from the following ingredients:

|  | Gm. |
|---|---|
| 2,5-bis allylamino-1,3,4-thiadiazole | 2500 |
| Lactose, U.S.P. | 1000 |
| Starch, U.S.P. | 300 |
| Talc, U.S.P. | 65 |
| Calcium stearate | 25 |

The thiadiazole compound is mixed with the starch lactose mixture followed by the talc and calcium stearate. The final mixture is then encapsulated in the usual manner. Capsules containing 10, 25, 50 and 100 mg. of active ingredient are also prepared by substituting 100, 250, 500 and 1000 gm. for 2500 gm. in the above formulation.

3. Soft elastic capsules — One-piece soft elastic capsules for oral use, each containing 500 mg. of active material are prepared in the usual manner by first dispersing the active material in sufficient corn oil to render the material capsulatable.

4. Aqueous suspension — An aqueous suspension for oral use containing in each 5 ml., 1 gm. of active ingredient is prepared from the following ingredients:

|  | Gm. |
|---|---|
| 2,5-bis ethylamino-1,3,4-thiadiazole | 2000 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D. & C. orange dye | 7.5 |
| Deionized water, q.s. to 10,000 ml. | |

What is claimed is:

1. A method of treating inflammation which comprises the administration to a patient in need of such treatment of an effective amount of a compound selected from the group consisting of 2,5-bis(ethylamino)-1,3,4-thiadiazole and 2,5-bis-(allylamino)-1,3,4-thiadiazole.

2. The method of claim 1 wherein the compound is 2,5-bis(ethylamino)-1,3,4-thiadiazole.

3. The method of claim 2 wherein the compound is 2,5-bis(allylamino)-1,3,4-thiadiazole.

* * * * *